US012496207B2

(12) United States Patent
Mitchell et al.

(10) Patent No.: US 12,496,207 B2
(45) Date of Patent: Dec. 16, 2025

(54) ORTHOTIC BRACE AND CLIP ATTACHMENT MECHANISM

(71) Applicant: MD Orthopaedics, Inc., Wayland, IA (US)

(72) Inventors: Lucas J. Mitchell, Wayland, IA (US); Marcus William Powell, New London, IA (US); Shawn Edward Twyman, Mt. Pleasant, IA (US)

(73) Assignee: MD Orthopaedics, Inc., Wayland, IA (US)

( * ) Notice: Subject to any disclaimer, the term of this patent is extended or adjusted under 35 U.S.C. 154(b) by 0 days.

(21) Appl. No.: 18/714,814

(22) PCT Filed: Nov. 30, 2022

(86) PCT No.: PCT/US2022/051446
§ 371 (c)(1),
(2) Date: May 30, 2024

(87) PCT Pub. No.: WO2023/102075
PCT Pub. Date: Jun. 8, 2023

(65) Prior Publication Data

US 2025/0025323 A1 Jan. 23, 2025

Related U.S. Application Data

(60) Provisional application No. 63/340,204, filed on May 10, 2022, provisional application No. 63/284,413, (Continued)

(51) Int. Cl.
*A61F 5/01* (2006.01)

(52) U.S. Cl.
CPC .................................. *A61F 5/0111* (2013.01)

(58) Field of Classification Search
CPC .... A61F 5/0193; A61F 5/0116; A61F 5/0127; A61F 5/0111; A61F 5/0113;
(Continued)

(56) References Cited

U.S. PATENT DOCUMENTS 3,931,817 A * 1/1976 Infranca ................ A61F 5/0193 602/24
5,470,310 A * 11/1995 Sutcliffe ............... A61F 5/0193 128/882
(Continued)

*Primary Examiner* — Kari K Rodriquez
(74) *Attorney, Agent, or Firm* — Gerald W. Roberts; John V. Daniluck; Dentons Bingham Greenebaum LLP

(57) ABSTRACT

A sole attachment assembly for attachment to an orthotic bar having a sole to retain a shoe of a user and a quick release member to couple to an orthotic bar. The sole includes a sole body, a release member receiver, a platform on the receiver, guide wings, a centering projection, and a release button barrier spanning between the guide wings. The quick release member includes a release member body, wings extending laterally from the release member body to slide within the guide wings, a locking tab to keep the quick release member coupled to the shoe sole by interfacing with the quick release button barrier, a locating recess in a top portion of the body configured to provide enhanced stability by interfacing with the platform on the sole, and a centering notch at the front of the body configured to interface with the centering projection on the sole.

17 Claims, 12 Drawing Sheets

Related U.S. Application Data filed on Nov. 30, 2021, provisional application No. 63/284,411, filed on Nov. 30, 2021.

(58) Field of Classification Search
CPC ...... A61F 5/3753; A61F 5/3715; A43B 13/28; A43B 13/30; A44B 11/2526; A44B 11/253; A44B 11/2584; A44B 11/2592; A44B 11/263; A44B 11/266
See application file for complete search history.

(56) References Cited

U.S. PATENT DOCUMENTS

| | | | | |
|---|---|---|---|---|
| 5,851,194 | A * | 12/1998 | Fratrick ................ | A61F 5/0127 24/625 |
| 7,267,657 | B1 * | 9/2007 | Mitchell ............... | A61F 5/0193 602/29 |
| 7,645,251 | B2 * | 1/2010 | Hatton .................. | A61F 5/0193 36/144 |
| 10,045,874 | B2 * | 8/2018 | Grosland ................. | A43B 7/00 |
| 10,314,730 | B2 * | 6/2019 | Connolly .............. | A61F 5/0116 |
| 2003/0154631 | A1 * | 8/2003 | Hirayama ............ | A43C 11/146 36/117.1 |
| 2007/0142760 | A1 * | 6/2007 | Mitchell ............... | A61F 5/0111 602/29 |
| 2012/0035520 | A1 * | 2/2012 | Ingimundarson ..... | A61F 5/0195 602/23 |
| 2014/0123440 | A1 * | 5/2014 | Capra ....................... | A61F 5/01 29/3 |
| 2016/0067075 | A1 * | 3/2016 | Malinowski .......... | A61F 5/0113 602/28 |

* cited by examiner

ORTHOTIC BRACE AND CLIP ATTACHMENT MECHANISM

CROSS-REFERENCE TO RELATED APPLICATIONS

This application is an International Patent Application that claims priority to and incorporates by reference in their entireties each of the following: U.S. Provisional Application No. 63/284,411, filed on Nov. 30, 2021, entitled "UNITARY INJECTION MOLDED BAR FOR CORRECTING CLUBFOOT;" U.S. Provisional Application No. 63/284,413, filed on Nov. 30, 2021, entitled "ORTHOTIC BRACE AND CLIP ATTACHMENT MECHANISM;" and U.S. Provisional Application No. 63/340,204, filed on May 10, 2022, entitled "UNITARY INJECTION MOLDED BAR FOR CORRECTING CLUBFOOT."

BACKGROUND

Dr. Ignacio Ponseti is an internationally famous physician and surgeon specializing in the treatment and management of a childhood deformity commonly known as a clubfoot. Dr. Ponseti has for many decades promoted the use of a foot and ankle abduction device, or orthosis, which is used to correct and prevent relapses of the clubfoot deformity. These abduction devices typically consist of a linear, rigid bar connected between shoes worn by the child which the bar separates the feet of the child and holds the feet in an outward rotation or abduction. Typically, if the condition is diagnosed early enough, this device is worn full-time for a period of months, but during the period of treatment, the angle of outward rotation is periodically adjusted using rotatable attachments, which may be screwed into a fixed engagement with the ankle and foot brace/orthotic or clipped into engagement with an attachment clip mechanism that itself is affixed to the linear, rigid bar and the ankle and foot orthotic.

The technique for treating clubfoot developed by Dr. Ponseti has become known throughout the world and has been highly successful in treating club feet without the necessity of corrective surgery. Many devices have been designed and used in performing Dr. Ponseti's technique. Some currently used devices that are used to perform Dr. Ponseti's manipulative technique are shown in U.S. Pat. No. 7,267,657, the disclosure of which is hereby incorporated by reference in its entirety. In the '657 patent there are disclosed devices which provide for release of the mounts from the abduction bar and universal mounts that can be attached to any shoe. The devices of the '657 patent and those typically used in Dr. Ponseti's clubfoot correction technique employ a rigid, typically multi component and metal shoe separating bar. The orthosis clip described in the '657 patent, in its typical arrangement, is affixed to the rigid linear bar using a screw or other fastening system that engages at three locations, one in the center and two proximate the circumference of a circular end of the rigid linear bar.

SUMMARY

One aspect of the present disclosure includes a quick release member for attachment to a sole of an orthotic shoe having a body to be coupled to an orthotic bar assembly for keeping the feet of a user at a predetermined distance, a pair of wings extending laterally from the body to slide within corresponding overhangs on the bottom of a shoe sole, a locking tab configured to keep the quick release member coupled to the shoe sole by interfacing with a quick release button barrier on the shoe sole, a locating recess in a top portion of the body configured to provide enhanced stability by interfacing with a platform on the shoe sole, and a notch, typically a centering notch, at the front of the body configured to interface with a centering projection on the shoe sole.

Another aspect of the present disclosure includes a sole attachment assembly for attachment to an orthotic bar having a sole to retain a shoe of a user and a quick release member to couple to an orthotic bar. The sole includes a sole body, a release member receiver, a platform on the receiver, guide wings, a centering projection, and a release button barrier spanning between the guide wings. The quick release member includes a release member body, wings extending laterally from the release member body to slide within the guide wings, a locking tab to keep the quick release member coupled to the shoe sole by interfacing with the quick release button barrier, a locating recess in a top portion of the body configured to provide enhanced stability by interfacing with the platform on the sole, and a centering notch at the front of the body configured to interface with the centering projection on the sole.

Yet another aspect of the present disclosure includes a method of attaching a quick release member to a sole for attachment to an orthotic bar to treat clubfoot, typically treating clubfoot using Dr. Ponseti's method of treating clubfoot, including the steps of sliding a pair of wings extending laterally from a body of a quick release member into a space formed by a pair of guide walls on the bottom of a sole, stabilizing the quick release member connection to the sole by interfacing a locating recess on the top of the body of the sole and platform on the bottom of the sole, centering the quick release member relative to the sole by interfacing a centering projection and a centering notch, locking the quick release member to the sole by sliding a locking tab on the quick release member past a release button barrier spanning across the pair of guide walls such that the locking tab is urged into an unlocking position until the locking tab slides past the release button barrier and creates an interference between the locking tab and the release button barrier, and releasing the quick release member from the sole by pushing by hand and without the use of tools the locking tab into a release position such that the locking tab and the release button barrier are no longer in interference with one another and sliding the quick release member out of the sole.

Yet another aspect of the present disclosure includes a method of attaching a quick release member to a sole for attachment to an orthotic bar to treat clubfoot including the steps of sliding a pair of guide walls on the bottom of a sole over a pair of wings extending laterally from a body of a quick release member, stabilizing the quick release member connection to the sole by interfacing a locating recess on the top of the body of the sole and platform on the bottom of the sole, centering the quick release member relative to the sole by interfacing a centering projection and a centering notch, locking the sole to the quick release member by sliding a release button barrier spanning across the pair of guide walls past a locking tab on the quick release member such that the locking tab is urged into an unlocking position until the release button barrier slides past the locking tab and creates an interference between the locking tab and the release button barrier, and releasing the quick release member from the sole by pushing by hand and without the use of tools the locking tab into a release position such that the locking tab and the release button barrier are no longer in interference with one another and sliding the sole away from the quick release member.

Another aspect of the present disclosure is generally directed to a quick release member for attachment to a sole of an orthotic shoe and an orthotic bar that includes: a main body adapted to be coupled to an orthotic bar assembly the main body having a top surface and a bottom surface, orthotic bar facing surface; an orthotic shoe clip portion that engages an orthotic shoe in use wherein the orthotic shoe clip portion has a first wing and a second wing that each extend laterally away from the main body and connect with a locking tab base portion that extends between a distal end of the first wing and a distal end of the second wing; a locking tab spaced between the first wing and the second wing and engaged with the locking tab base portion and the locking tab is biased at an angle such that it is not in the same plane as a plane defined by the first wing and the second wing; and at least one notch within the locking tab base portion.

These and other aspects, objects, and features of the present disclosure will be understood and appreciated by those skilled in the art upon studying the following specification, claims, and appended drawings.

DETAILED DESCRIPTION

Figure 1:
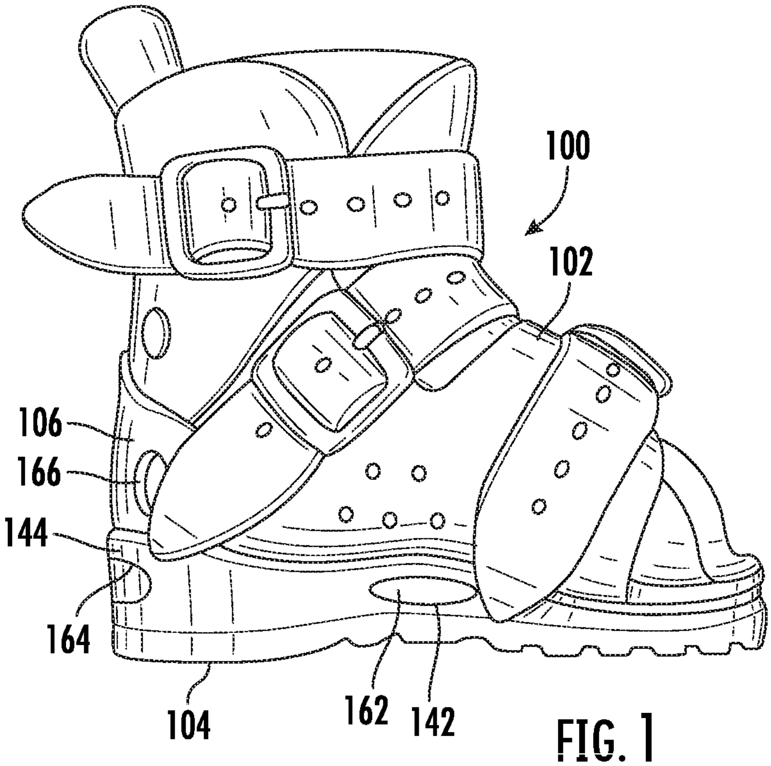
FIG. 1 is an elevated side view of an article of footwear of an aspect of the present disclosure used in connection with the treatment of clubfoot.

For purposes of description herein, the terms "upper," "lower," "right," "left," "rear," "front," "vertical," "horizontal," and derivatives thereof shall relate to the disclosure as oriented in FIG. 1. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Now referring to the drawings wherein like numerals refer to like matter throughout, and more specifically referring to FIG. 1, there is shown an article of footwear 100, according to an aspect of the present disclosure. Footwear 100 is shown having an upper 102, which could be any type of wearable material, but is typically leather, fabric, vinyl or other material suitable for a shoe or sandal. Footwear 100 further includes a sole 104, which is typically a single molded piece of plastic material, such as a flexible polymer. Other material suitable for shoe or sandal soles could be used as well. Also shown in FIGS. 1-5 is insole 106, which is disposed above upper 102 and generally within upper 102. Typically, insole 106 is a single piece of molded polyurethane or rubber-like material. Typically, insole 106 is pliable enough so as to permit it to conform to the shape of a child's foot when inserted therein and secured thereon by upper 102. The insole 106 is also sufficiently soft and pliable to be comfortable for the child to wear without injury or irritating the child's skin.

Insole 106 is typically secured to sole 104 by glue and may be supplemented, if necessary, providing an insole side protuberance 162 to extend through a sole side hole 142 in sole 104. While one insole side protuberance is shown it should be appreciated that a plurality of spaced apart and/or differently shaped protuberances may be used and mated with corresponding side holes. Similarly, insole heel protuberance 164 extends through sole heel hole 144 and thereby holds insole 106 stable with respect to sole 104. Again, while one insole heel protuberance is shown multiple protuberances with the same or different shapes could be used and engaged with the sole heel holes. Insole 106 is also shown having an insole heel right viewing hole 166, which is located near the heel of the insole 106, so that it can readily be seen that a child's foot is in contact with the insole 106. In a preferred embodiment, the insole heel right viewing hole 166 is a pair of holes on opposite sides of the heel or is a single hole which spans to both sides of the heel. In either embodiment, it would be possible to view the placement of the child's foot with respect to the insole 106 from a vantage point on either side of the heel.

Figure 2:
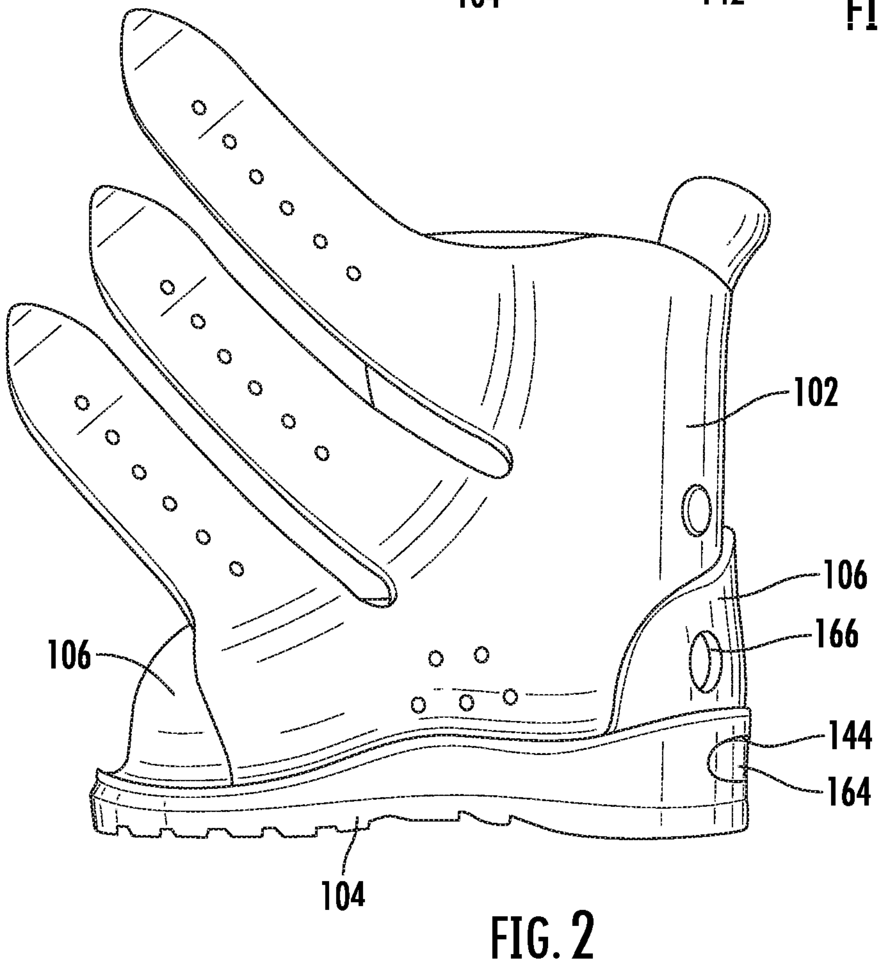
FIG. 2 is an elevated side to rear view of the shoe of FIG. 1 with the straps elevated for display purposes in a disengaged position.

Now referring to FIG. 2, there is shown an opposite side of footwear 100 of FIG. 1 in an unbuckled position. The footwear 100 is shown using buckles, but the footwear 100 may be enclosed on a child's foot using another attachment system such as a hook and loop fastening system or even a tie system, but a tie system is not typically employed because they are hard for the child to attach. Moreover, the hook and loop fastener engagement system is sometimes disadvantageous because young children may be able to open the footwear when they should not.

Figure 3:
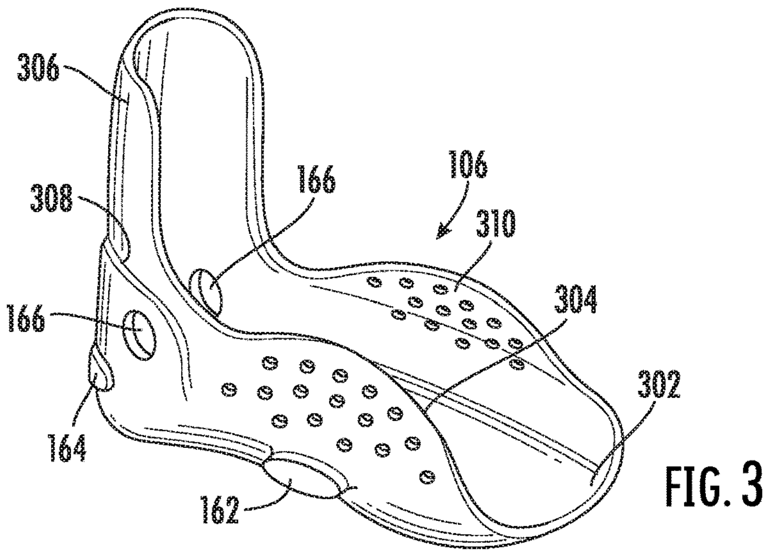
FIG. 3 is a perspective view of the in-foot cradle of FIG. 1 of according to an aspect of the present disclosure.

Now referring to FIG. 3, there is shown a perspective view of the insole 106 of FIG. 1 when it is separated from footwear 100. Insole 106 is shown having an insole toe end 302 and an insole sole foot side 304. Preferably, insole sole foot side 304 is generally a flat surface without substantial contours to fit to an arch of a foot. Insole 106 includes an insole heel and ankle support 306 with an insole strap support 308, which keeps an ankle support strap from slipping downward. Insole 106 further includes insole side wall 310 on opposing sides of insole sole foot side 304. In a preferred embodiment, insole sole foot side 304, insole side wall 310 and insole heel and ankle support 306 all are portions of a single molded piece of urethane, pliable rubber-like material or flexible polymer material.

Figure 4:
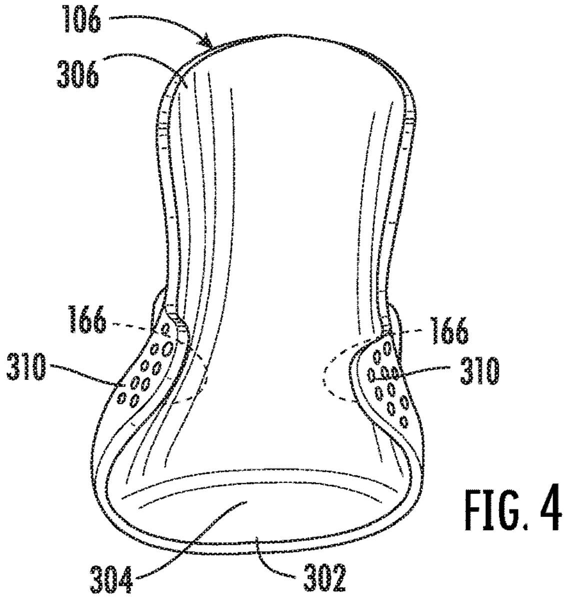
FIG. 4 is an elevated front view of the foot cradle of FIG. 3.
Figure 5:
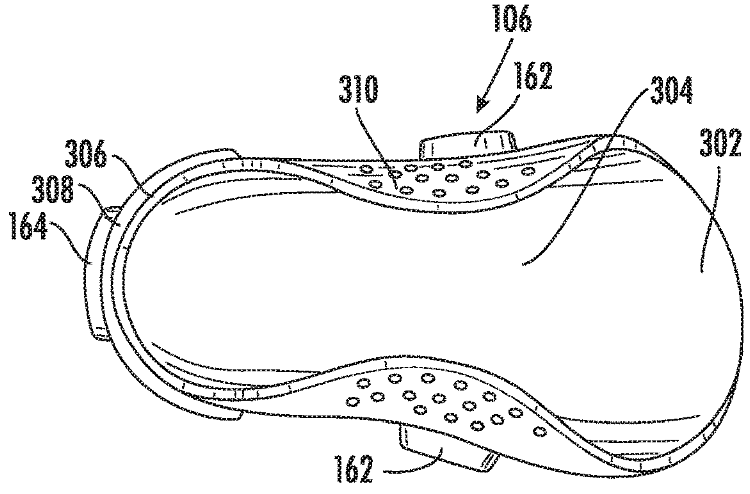
FIG. 5 is a top view of the foot cradle of FIG. 4.

Now referring to FIGS. 4 and 5, there are shown front and top views, respectively of the insole 106 of FIGS. 1, 2 and 3.

Figure 6:
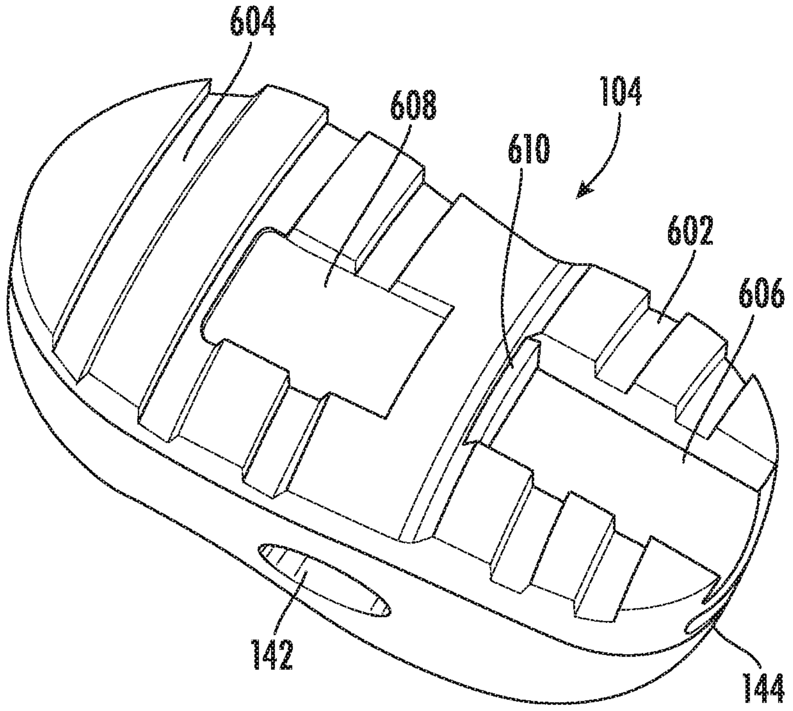
FIG. 6 is a bottom perspective view of the sole portion of the shoe of FIG. 1 according to an aspect of the present disclosure.

Now referring to FIG. 6, there is shown a perspective view of the bottom of sole 104 of the footwear 100 from FIG. 1. Sole heel 602 is shown disposed at an opposite end of sole 104 from sole toe end 604. Sole heel 602 has at least one sole attachment receiving groove 606 therein, which is separated from quick release push button receiving void 608 by quick release button barrier 610. Preferably, all of these features, sole heel 602, sole toe end 604, sole attachment receiving groove 606, quick release push button receiving void 608 and quick release button barrier 610, are integrally formed in a single piece of durable plastic or other material suitable for a rigid shoe sole. This material may need to be more rigid than a typical shoe sole material because of the need for increased lateral forces owing to the use of the splint between the shoes. The quick release push button engagement system engages the quick release member, which has quick release button 708 (See FIGS. 7, and 10-14) that engages the quick release push button receiving void 608.

Figure 7:
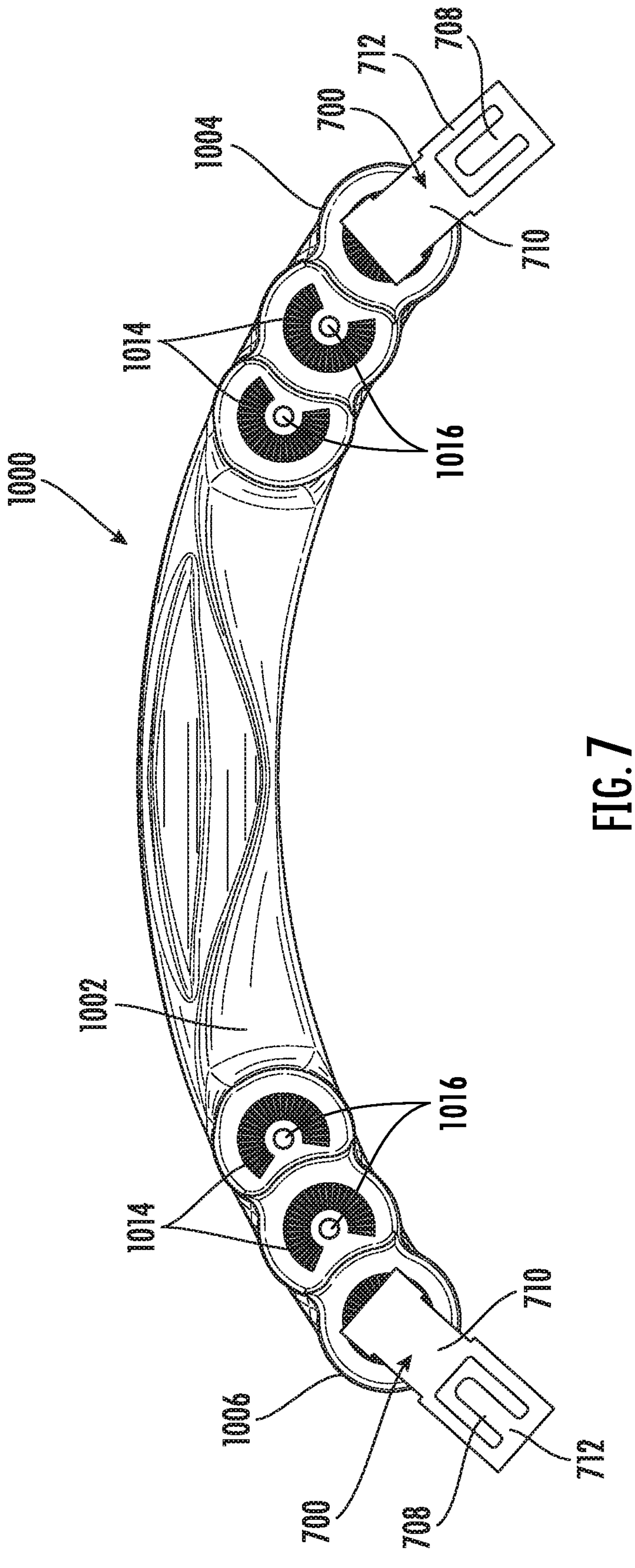
FIG. 7 is top view of a bar assembly according to an aspect of the present disclosure.
Figure 8:
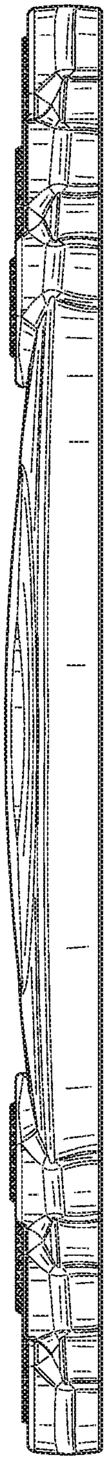
FIG. 8 is a front view of a bar according to an aspect of the present disclosure.
Figure 9:
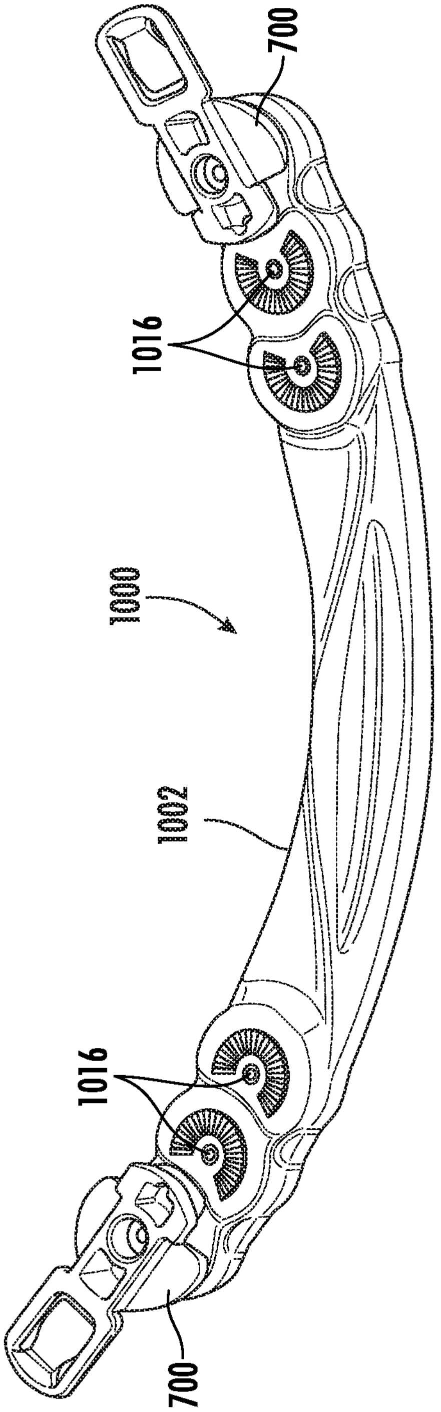
FIG. 9 is an elevated front view of a bar assembly according to an aspect of the present disclosure.

FIGS. 7-9 show an adjustment bar assembly 1000. The bar assembly 1000 may include a bar 1002, and a pair of quick release members 700. The bar 1002 shown in the figure is a unitary, integral bar that is typically an injection molded plastic material. However, other orthotic bars for the treatment of clubfoot may be used with the quick release members 700 of the present disclosure. One example is the bar and attachment system shown in FIGS. 17-18 and discussed in more detail later herein. The bar 1002 may include a first end 1004 and a second end 1006. Each of first and second ends 1004, 1006 may include a plurality of locating positions. FIGS. 7-9 show three locating positions on each end 1004, 1006. These include an inner locating position 1008, an intermediate locating position 1010, and an outer locating position 1012. The locating positions may be offset in height as shown in FIG. 8, or they may all share a common plane, they all may be oblique to one another, or any other arrangement desired.

The quick release member 700 is typically attached to a bar using a fastener, typically a threaded fastener such as a screw or bolt, more typically a medical grade screw or bolt, through a single connection hole 1016. Each connection hole typically includes a threaded metal sleeve positioned within the aperture 1016 that typically engages a screw through the quick release member 700 and into the threaded receiving aperture. The threaded metal sleeve(s) are typically integrally formed into the bar. The female threaded metal sleeve positioned within the aperture is typically formed by molding the bar 1000 around the metal threaded screw receiving aperture 1016. Each single connection hole 1016 is typically positioned co-centric with a plurality of ribs 1014 that extend around a majority or the entirety of an aperture 1016 of the bar 1000 and extend upward from the top surface of the bar such that the ribs create ridges and valleys. These ribs 1014 may be used to adjust the angle of the quick release member and thereby the angle of the shoes when engaged with the quick release member during treatment. The ribs 1014 may engage corresponding ridges 1751 on the bottom surface of the quick release member to further retain the quick release member more securely in the correct treatment position and be easily adjustable across a range of positions.

The adjustment bar assembly 1000 further includes quick release members 700, which are configured to be inserted into sole attachment receiving groove 606 and quick release push button receiving void 608 of FIG. 6. The quick release members 700 may have main body 712 that extends outwardly from a base portion 710. The quick release main body 712 is configured to fit into sole attachment receiving groove 606 and slide in further until quick release button 708 snaps into a locked position in quick release push button receiving void 608. Quick release button 708 is preferably biased outwardly or downwardly (in the orientation of FIG. 10) by a spring-like structure or arrangement, such as a living hinge or an external spring.

As the quick release member 700 is inserted into the sole 104, the quick release button barrier 610 interfaces with the quick release button 708 in the following way. The quick release button 708 slides along the quick release button barrier 610, increasingly pushing against its bias until the quick release member 700 reaches substantially its home position within the sole 104. Once the quick release button 708 clears the quick release button barrier 610, the quick release button 708 snaps back into its biased and default position thereby providing interference with the quick release button barrier 610 such that the quick release member cannot be removed from the sole 104 until a user positively pushes to apply force against the quick release button 708 below the quick release button barrier 610, and the quick release member 700 can slide out of the sole 104. Typically, the force used to depress the quick release button sufficient to release it from engagement with the sole of the orthotic shoe is greater than what a child can apply, typically a child that is four years old or less. The force needed to depress the quick release button 708, which may be a "tab" as shown, is typically greater than 16 Newtons, more typically greater than about 25 Newtons, and more typically greater than 35 Newtons. The force may be adjusted, but is typically high enough that a child being treated for clubfoot can not remove the quick release member 700 from engagement with the orthotic footwear without the assistance of someone older, preferably an adult. Surface 714 typically engages an orthotic bar of the present disclosure when in use.

The quick release members 700 may be attached to the adjustment bar 1000 at the connection holes 1016. The quick release members 700 may include a threaded stud, a screw, a bolt, or other fastener that extends through or into the connection hole 1016, and is attached by a nut on the opposite side of the bar 1000. The nut is attached to the end of the stud and tightened until it applies pressure against the bottom side of the bar 1000. It should be noted that the bolt and nut combination may be reversed, i.e. the bolt may be integral with the bar 1000, or the bolt may be a completely separate member from the quick release member 700 and extend through a corresponding hole in the quick release member 700.

In operation, the present devices can be used to carry out the technique of Dr. Ponseti to treat clubfoot according to the process discussed below. A practitioner determines the proper spacing and angle for a user's feet using any method known in the art. The practitioner then attaches one of the quick release members 700 to the bar 1000 by inserting the integrally coupled bolt through the locator hole 1016. A nut is attached on the opposite side of the bar from the quick release member 700, but not tightened. The practitioner then orients the quick release member at the desired angle. The nut is then tightened down. As the bolt is tightened down, the ribs 1014 of the quick release member interfere with the ribs on the bar 1000, preventing rotation of the quick release member 700 with respect to the bar 1000. The practitioner then attaches the second quick release member 700 to the other end of the bar 1000 in the same way.

The practitioner then places the shoes or footwear 100 on the user's feet. Each of the shoes 100 are placed over the quick release members 700 by sliding the quick release main body into sole attachment receiving groove 606 on the footwear 100 and sliding in further until quick release button 708 snaps into a locked position in quick release push button receiving void 608.

It should be noted that the attachment described above may further be accomplished in alternate steps without deviating from the spirit of the disclosure. For instance, the footwear 100 may be attached to the user first and quick release members 700 slid into their respective receiving grooves 606 before attachment to the bar. The practitioner may then insert the bolts of the quick release into the locator holes 42 and tighten down. Further, there may be no bolts at all, but rather a quick-click style attachment or something similar known in the art.

Figure 10:
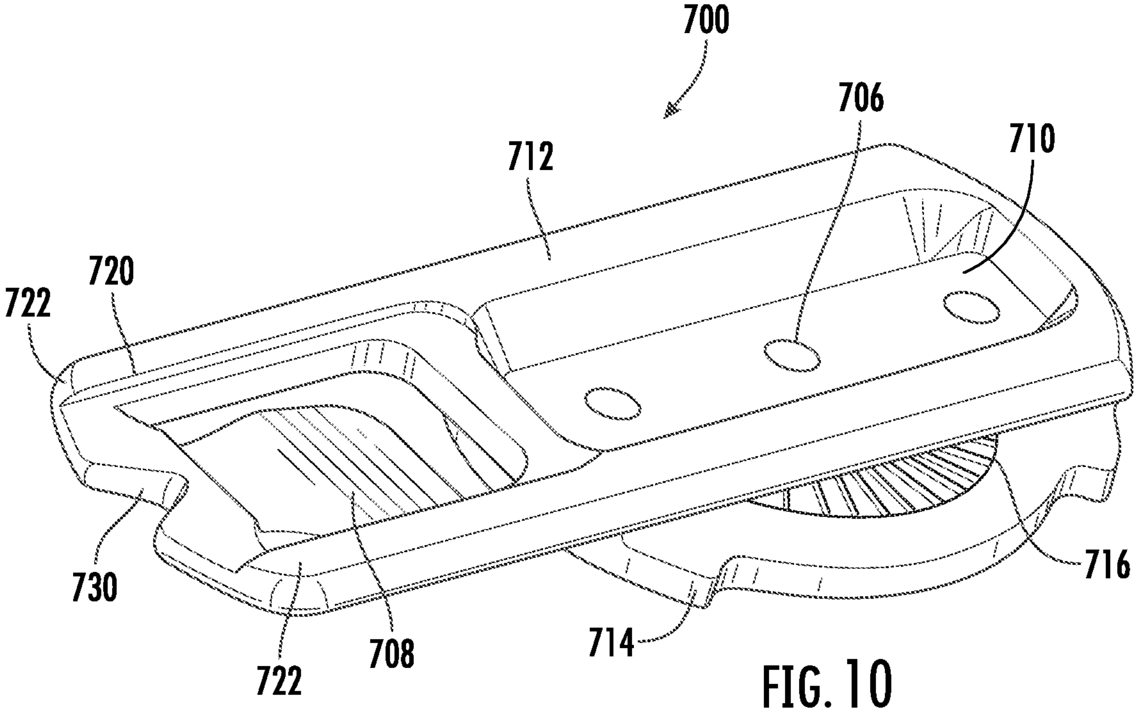
FIG. 10 is an elevated view of the top of a quick release member of an embodiment of the present disclosure.
Figure 11:
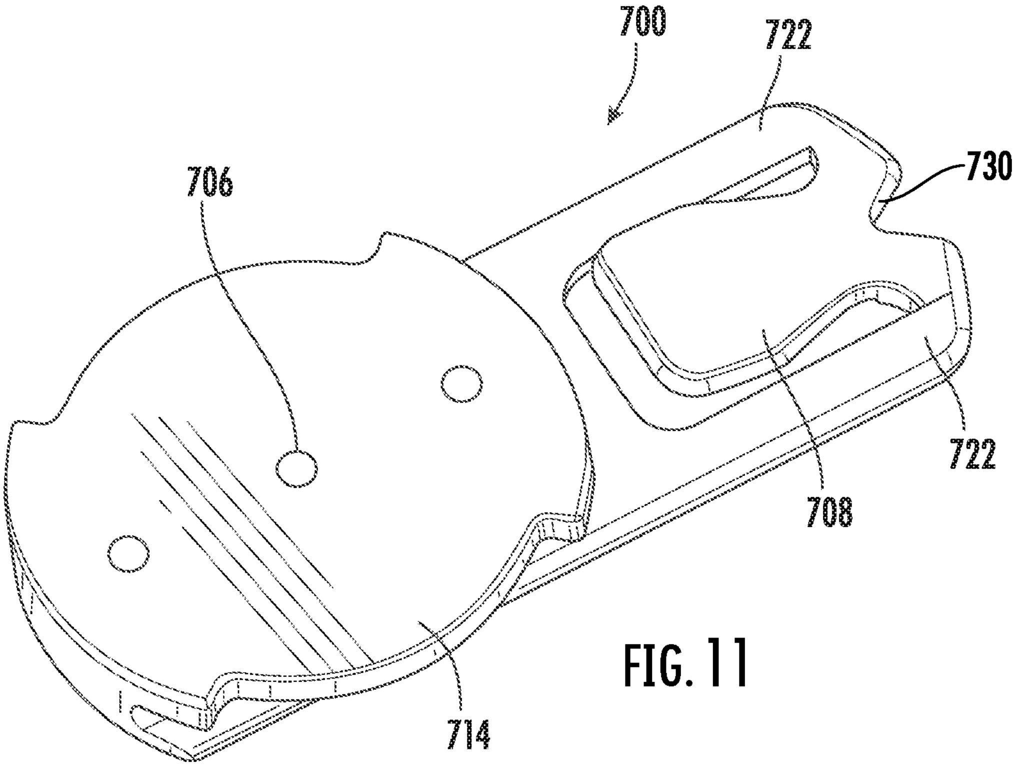
FIG. 11 is an elevated bottom view of a quick release member according to an aspect of the present disclosure.
Figure 12:
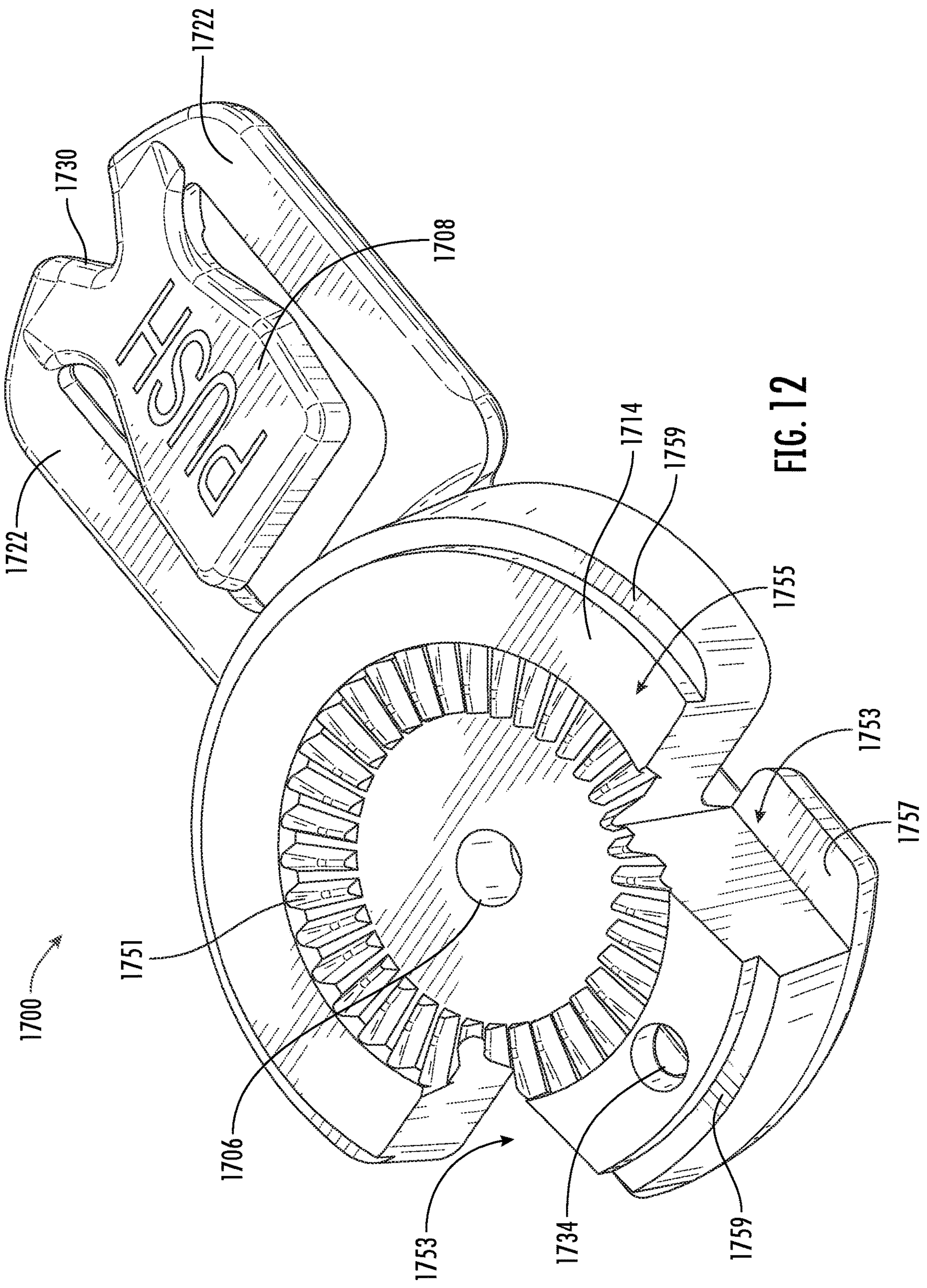
FIG. 12 is a bottom perspective view of a quick release member according to an aspect of the present disclosure.
Figure 13:
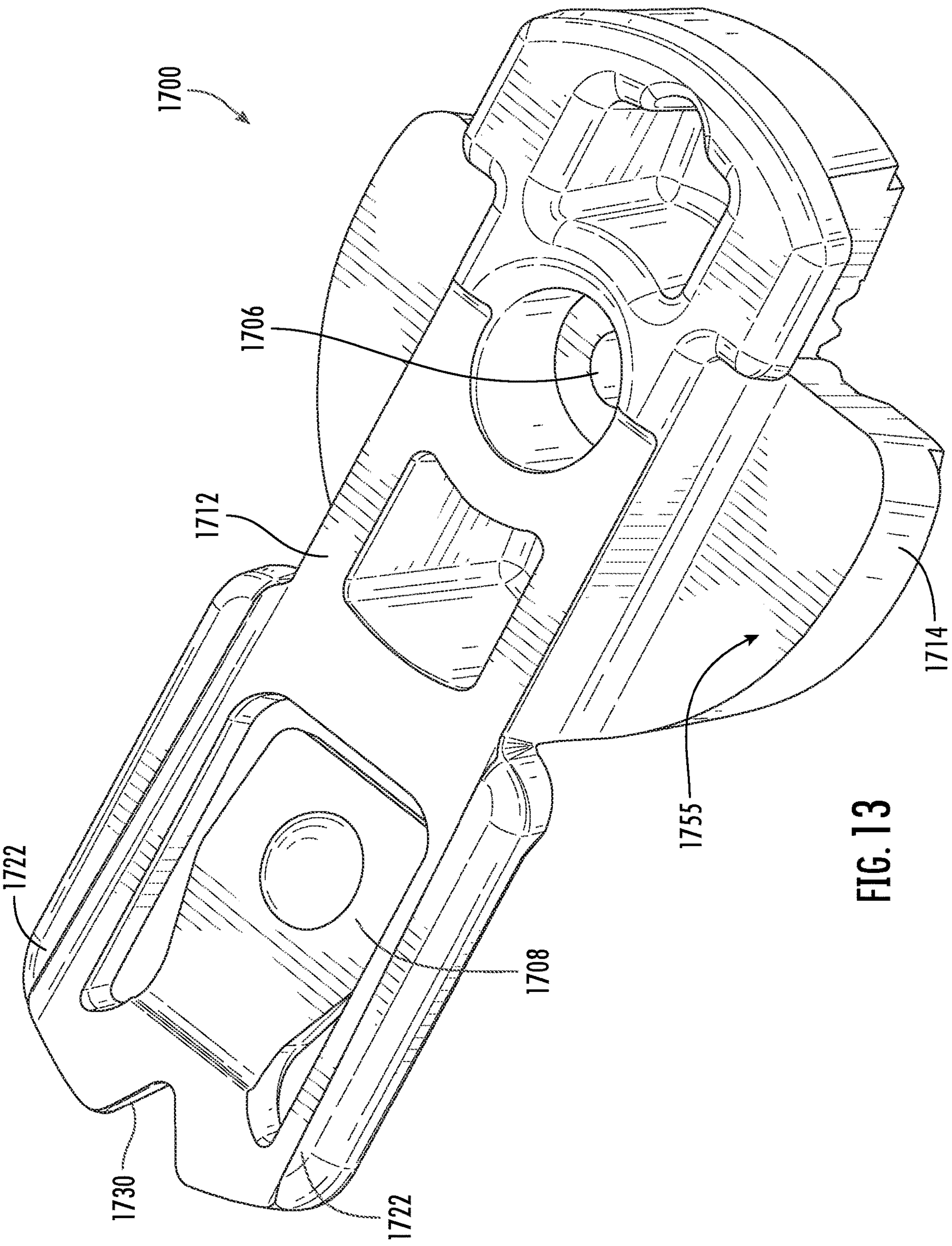
FIG. 13, is a top perspective view of a quick release member according to an aspect of the present disclosure.
Figure 14:
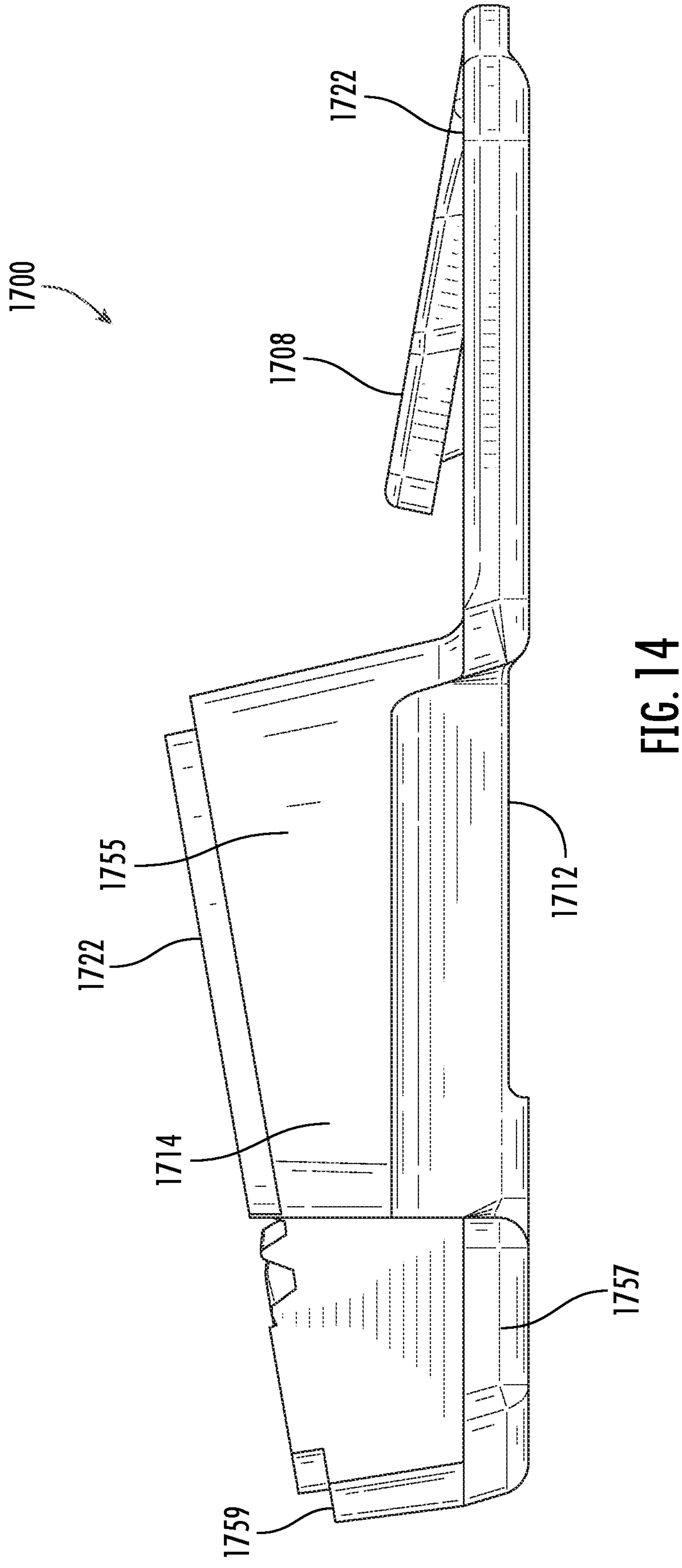
FIG. 14 is a side view of a quick release member according to an aspect of the present disclosure.
Figure 15:
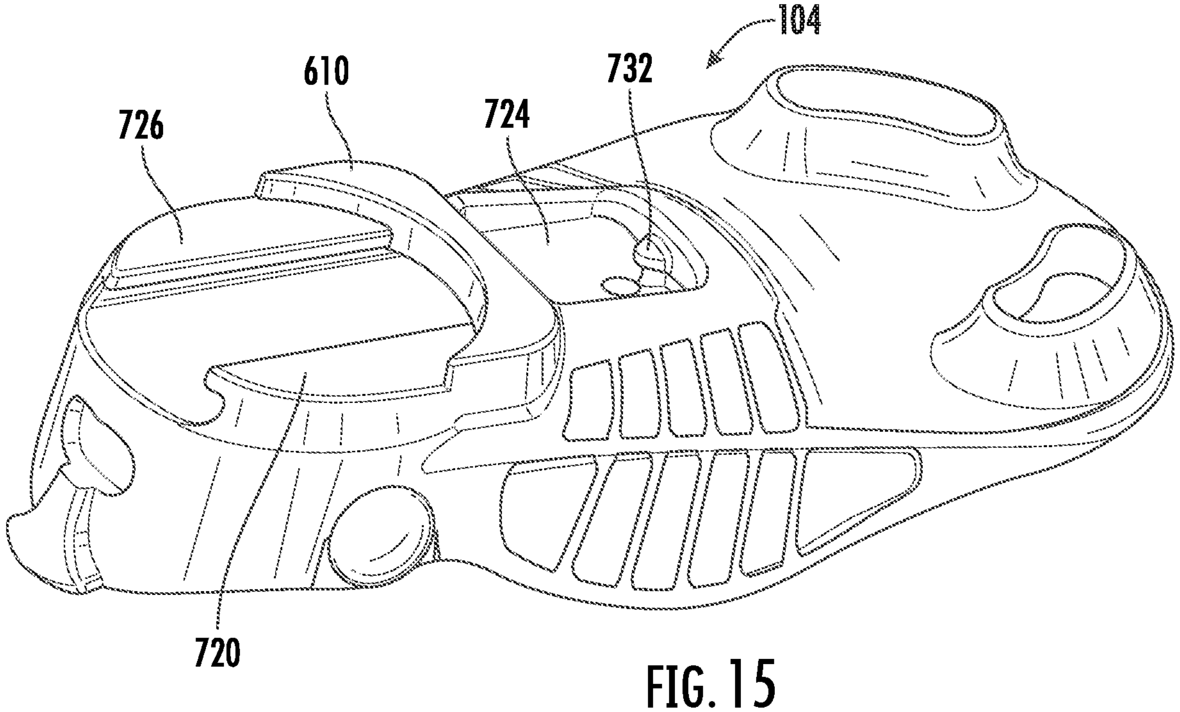
FIG. 15 is a bottom perspective view of a sole attachment base of an orthotic shoe for the treatment of clubfoot that may be used in conjunction with a quick release member according to an aspect of the present disclosure.
Figure 16:
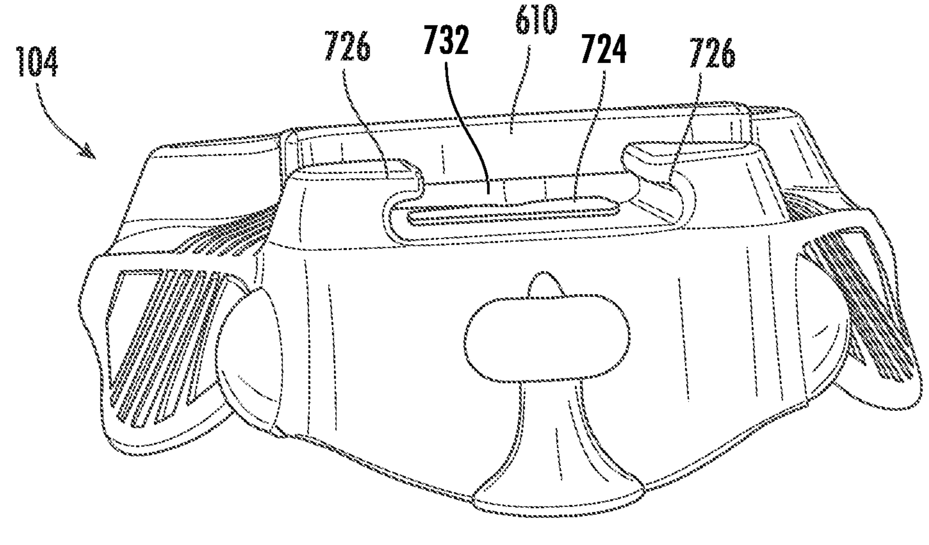
FIG. 16 is an inverted rear view of a sole attachment of an orthotic shoe for the treatment of clubfoot that may be used in conjunction with a quick release member according to an aspect of the present disclosure.

As shown in more detail in FIGS. 10-13, the quick release members 700 and the soles 104 may include elements that ensure that the connection between the quick release member 700 and the sole 104 is tight and reduces any "slop" or play between the two parts to a minimal amount. FIG. 10 shows a quick release member 700 that includes a locating indentation 720 that is cut within the top (as oriented in FIG. 10) locating wings 722. The locating wings 722 fit within a locating slot formed by overhangs 726 in the sole 104 (see FIG. 15). The overhangs 726 guide the locating wings 722 into place within the sole 104. The overhangs 726 overhang opposing sides of the space on the sole containing the platform 724 typically have a corresponding mating shape to the locating wings 722.

As the quick release member 700 gets closer to its home and locked position, the locating indentation 720 on the quick release member 700 interfaces with a platform 724 on the sole 104, and a centering notch 730 at the front or leading edge (as the quick release member 700 is inserted into the sole) of the quick release member 700 interfaces with a centering projection 732 on the sole. The platform 724 is typically spaced in the recess of the sole and typically integrally formed therein, but could conceivably be engaged as a separate component to the bottom of a footwear/orthotic. While shown as a rounded bump that is generally V-shaped, the platform 724 typically has a centering projection 732 on the end wall of the platform closest to the toe end of the footwear and projecting backward toward the heel of the footwear and toward the opposite end of the platform 724 that receives a portion of the quick release member including the locating wings 722 and the quick release button or tab. The projection can be any shape. There could also be more than one projection as well that are spaced apart from one another but on the end wall. In such instance, the at least one notch 730 would be designed to correspondingly mate with the projection thereon. This provides the quick release member 700 and the sole 104 with more surfaces and planes to interface and interact and substantially reduces the amount of play between the quick release member 700 and the sole 104, providing a more stable position for the user of the device.

The quick release members may further include a hole 706 within a counterbore, which is a cylindrical flat-bottomed hole that enlarges another coaxial hole. As the practitioner attached the quick release member 700 to the bar 1002 in this embodiment, a fastener such as a screw may be placed within the hole 706 and through the hole 1016 in the bar 1002. A nut may be placed on the bottom side of the bar 1002 and fastened to the screw to tighten the quick release member to the bar 1002 and keep it in place.

Another quick release member is shown in FIGS. 12-18. This quick release member may be used with most, if not all of the orthotic bars used to treat clubfoot and can be used with the bars shown in any of the figures of this application and described herein. The quick release member 1700 shown in FIGS. 12-18 of the present disclosure has a single center attachment hole 1706 and a hole 1734 that permits viewing through the quick release member to a surface on the other side of the viewer when viewed from either side of the quick release member. The ridges 1751 are radially distributed around the single center attachment hole 1706 on the surface 1714 of the quick release member. As can be seen in the drawings, the main body 1755 may have two cut our portions 1753 on either side of an end of the main body portion 1755 of the quick release member and a bottom shelf 1757 on both sides thereof. The main body 1755 is typically angular with the top surface 1714 of the main body extending at an elevated angle from the horizontal plane of the bottom surface of the main body. The elevated angle is typically from about 10 to about 15 degrees, more typically from 10 degrees to 15 degrees or exactly 10 degrees or 15 degrees. There is also typically a radial lip 1759 around the perimeter of the overall main body portion 1755.

Figure 17:
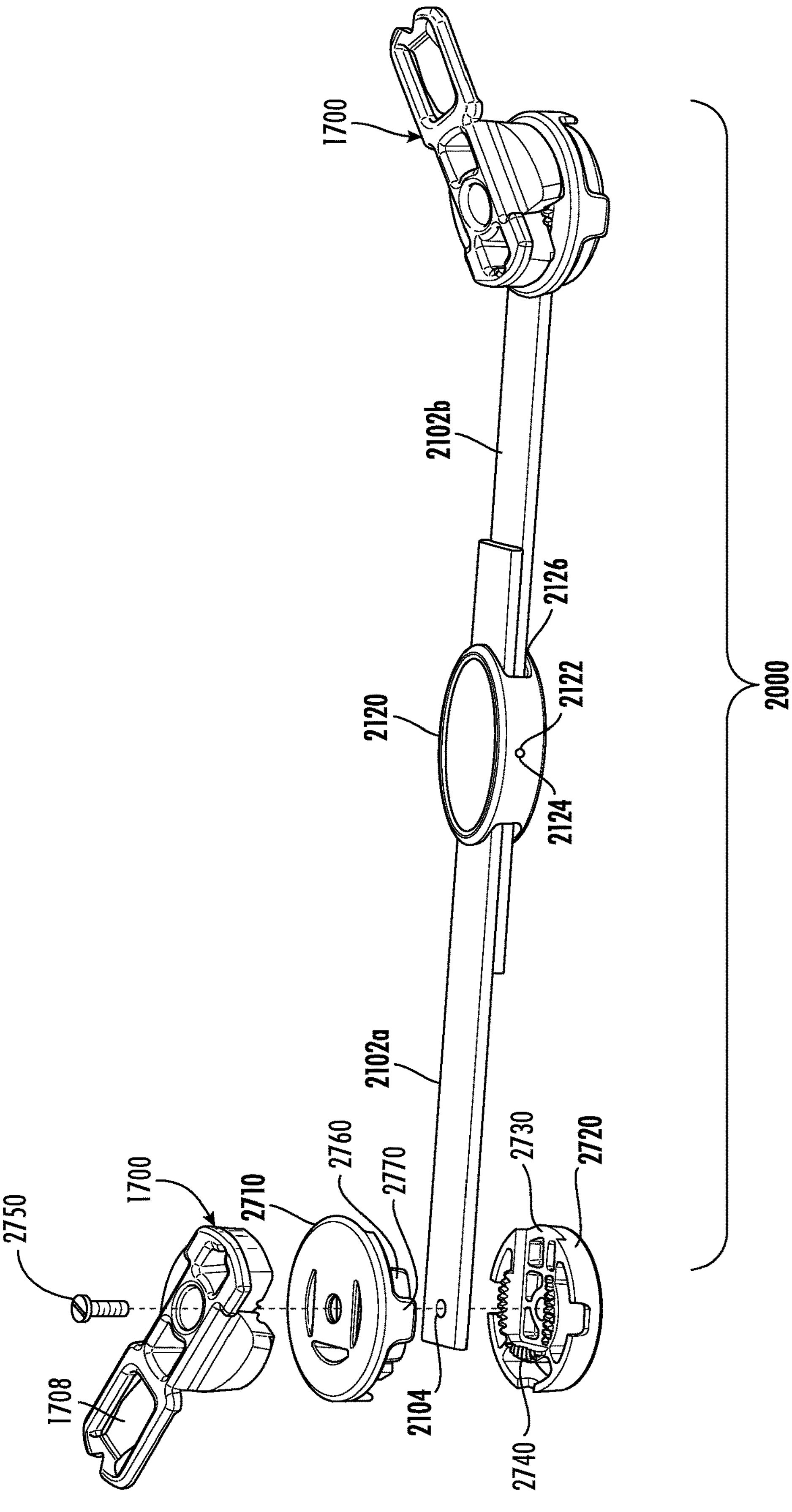
FIG. 17 is a partially exploded top perspective view of a quick release member engaged to an orthotic bar according to an aspect of the present disclosure.
Figure 18:
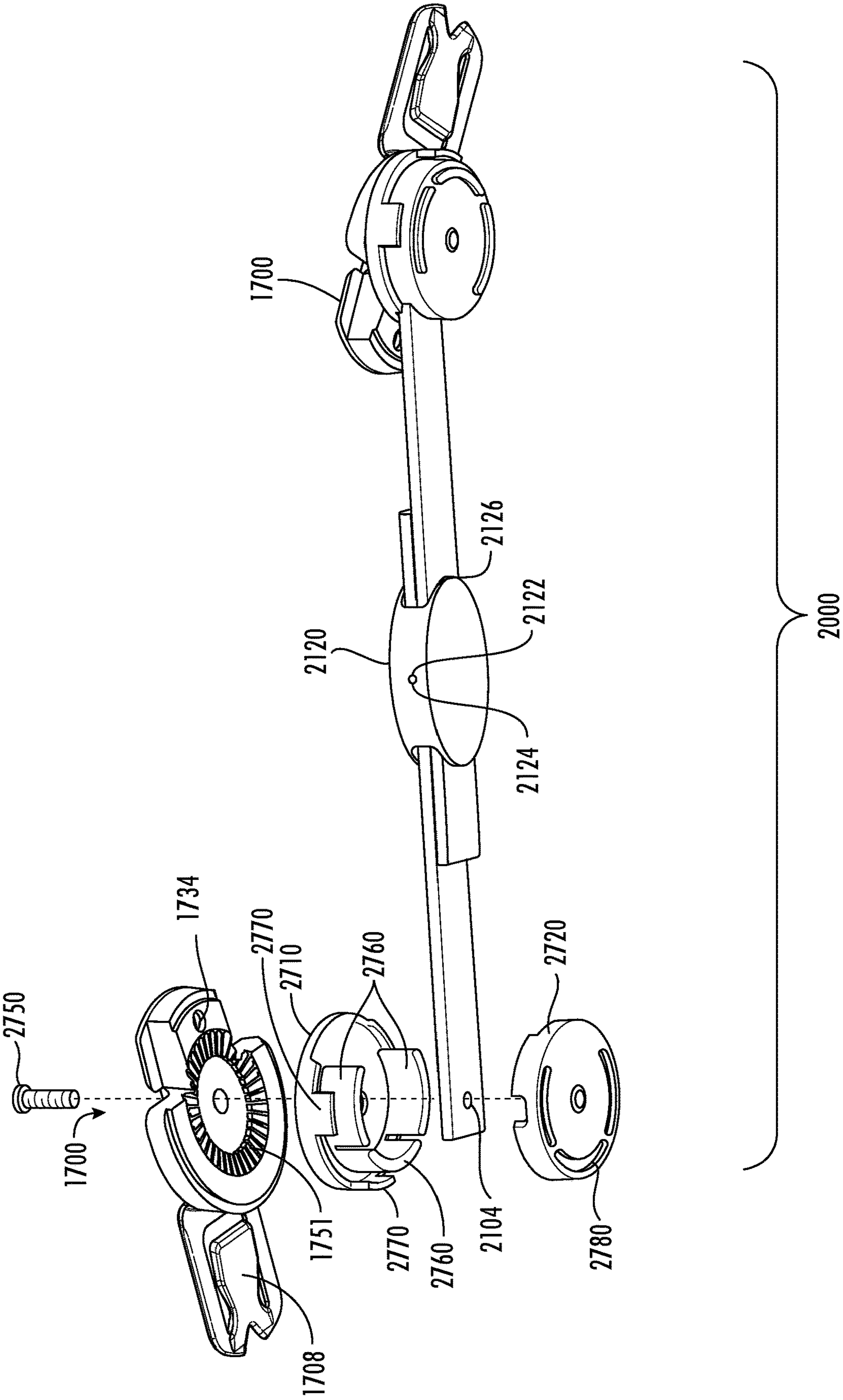
FIG. 18 is a partially exploded bottom perspective view of a quick release member engaged to an orthotic bar according to an aspect of the present disclosure.

Another adjustable bar and using a quick release member 1700 or other quick release member as described herein is shown in FIGS. 17-18 of the present disclosure. An adjustable bar 2102 is shown as two end bars 2012*a* and 2102*b*. The end bars 2102*a* and 2102*b* may be placed in an overlapping fashion and held in place by a bar lock 2120. The bar lock 2120 has a through slot 2126 that allows the end bars 2102*a* and 2102*b* to both fit within one on top of another. The bar lock 2120 may also include a threaded hole 2122 and a set screw 2124 therein. With the end bars 2102*a* and 2102*b* in place, the set screw 2124 may be tightened creating pressure on the bars 2102*a* and 2102*b*, forcing them against one wall of the through slot 2126, and holding them in place fixedly by the pressure applied by the set screw 2124. In this way, a practitioner may set one of any of a variety of lengths of the bar 2102 and customize for each user of the bar. The longest extent of the length of the adjustable bar 2102 would only be limited by the lengths of end bars 2102*a* and 2102*b*. The combined length may be adjusting the extent of the overlap of the bars 2102*a*, 2102*b*.

The quick clip members 1700 according to this aspect of the present disclosure may engage an intermediate portion 2710, which, in turn, engages a bottom portion 2720. The three components 1700, 2710, and 2720 may be assembled first and the angle of the quick clip member set with respect to the bottom portion 2720 before introducing the bar 2102 into the assembly. The assembly includes a slot 2730 into which the bar 2102 is placed, and a screw is tightened through the center holes of each part, through a hole 2104 of the bar 2102, and into a threaded portion of the bottom portion 2720. The intermediate portion may be a plastic material, but is most typically a thermoplastic elastomer (TPE), which is sometimes referred to as thermoplastic rubber, such that, when the intermediate portion 2710 is an elastomeric material, it provides higher friction and a better grip of the bar 2102 to prevent slippage during use if one wearing the device stands (see right side of assembly shown in FIG. 18). The intermediate portion 2710 typically has downwardly extending projection portions 2760, 2770 that extend through apertures the bottom portion and around the perimeter of the bottom portion to provide the gripping surface on the bottom thereof. The upwardly facing teeth 2740 on the inner portion of the bottom portion 2720 can function to grip the bottom surface of the intermediate portion 2710 and grip the elastomeric material. It should be known to one of ordinary skill that the bar may be placed into the bottom portion 2720 first and the intermediate portion 2710 and quick clip member 1700 then placed on top of the bar 2102 before tightening screw 2750 as well.

It will be understood by one having ordinary skill in the art that construction of the described disclosure and other components is not limited to any specific material. Other exemplary embodiments of the disclosure disclosed herein may be formed from a wide variety of materials, unless described otherwise herein.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the Applicant intends to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. An orthotic sole attachment assembly for attachment to an orthotic bar to treat clubfoot, the assembly comprising:

a sole adapted to accept and retain a shoe of a user, the sole including
- a sole body,
- a release member receiving portion,
- a platform on the release member receiving portion,
- a pair of guide wings,
- a centering projection, and
- a release button barrier spanning between the pair of guide wings; and a quick release member adapted to be coupled to an orthotic bar assembly for keeping feet of a user at a predetermined distance, the quick release member including
- a release member body,
- a pair of wings extending laterally from the release member body, the pair of wings configured to slide within the pair of guide wings on the sole,
- a locking tab configured to keep the quick release member coupled to the sole by interfacing with the release button barrier on the sole,
- a locating recess in a top portion of the release member body configured to provide enhanced stability by interfacing with the platform on the sole, and
- a centering notch at a front of the release member body configured to interface with the centering projection on the sole.

2. The orthotic sole attachment assembly of claim 1, wherein the release member body is coupled to the orthotic bar through a threaded fastener.

3. The orthotic sole attachment assembly of claim 2, wherein the threaded fastener is integrally formed with the quick release member.

4. The orthotic sole attachment assembly of claim 3, wherein the threaded fastener is overmolded by the quick release member.

5. The orthotic sole attachment assembly of claim 3, wherein the locking tab is biased in a downward direction.

6. The orthotic sole attachment assembly of claim 5, wherein the bias is induced by a living hinge integrally formed between the locking tab and the release member body.

7. The orthotic sole attachment assembly of claim 2, wherein the threaded fastener is overmolded by the quick release member.

8. The orthotic sole attachment assembly of claim 7, wherein the locking tab is biased in a downward direction.

9. The orthotic sole attachment assembly of claim 8, wherein the bias is induced by a living hinge integrally formed between the locking tab and the release member body.

10. The orthotic sole attachment assembly of claim 2, wherein the locking tab is biased in a downward direction.

11. The orthotic sole attachment assembly of claim 4, wherein the bias is induced by a living hinge integrally formed between the locking tab and the release member body.

12. The orthotic sole attachment assembly of claim 1, wherein the locking tab is biased in a downward direction.

13. The orthotic sole attachment assembly of claim 12, wherein the bias is induced by a living hinge integrally formed between the locking tab and the release member body.

14. A method of attaching a quick release member to a sole for attachment to an orthotic bar to treat clubfoot, comprising the steps of:

sliding a pair of wings extending laterally from a body of a quick release member into a space formed by a pair of guide walls on a bottom of a sole;

stabilizing a quick release member connection to the sole by interfacing a locating recess on a top of the body of the quick release member and a platform on the bottom of the sole;

centering the quick release member relative to the sole by interfacing a centering projection and a centering notch;

locking the quick release member to the sole by sliding a locking tab on the quick release member past a release button barrier spanning across the pair of guide walls such that the locking tab is urged into an unlocking position until the locking tab slides past the release button barrier and creates an interference between the locking tab and the release button barrier; and releasing the quick release member from the sole by pushing by hand and without the use of tools the locking tab into a release position such that the locking tab and the release button barrier are no longer in interference with one another and sliding the quick release member out of the sole.

15. The method of claim 14, wherein the centering step is performed by the centering projection on the sole and the centering notch on the quick release member.

16. A method of attaching a quick release member to a sole for attachment to an orthotic bar to treat clubfoot, comprising the steps of:

sliding a pair of guide walls on a bottom of the sole over a pair of wings extending laterally from a body of the quick release member;

stabilizing a quick release member connection to the sole by interfacing a locating recess on a top of the body of the quick release member and a platform on the bottom of the sole;

centering the quick release member relative to the sole by interfacing a centering projection and a centering notch;

locking the sole to the quick release member by sliding a release button barrier spanning across the pair of guide walls past a locking tab on the quick release member such that the locking tab is urged into an unlocking position until the release button barrier slides past the locking tab and creates an interference between the locking tab and the release button barrier; and releasing the quick release member from the sole by pushing by hand and without the use of tools the locking tab into a release position such that the locking tab and the release button barrier are no longer in interference with one another and sliding the sole away from the quick release member.

17. The method of claim 16, wherein the centering step is performed by the centering projection on the sole and the centering notch on the quick release member.

* * * * *